United States Patent [19]

Wolf

[11] 4,353,987

[45] Oct. 12, 1982

[54] PROCESS FOR PREPARING GLYCERALDEHYDE FROM GLYCEROL WITH METHANOL DEHYDROGENASE

[75] Inventor: Holly J. Wolf, Comstock Township, Kalamazoo County, Mich.

[73] Assignee: The Upjohn Company, Kalamazoo, Mich.

[21] Appl. No.: 272,625

[22] Filed: Jun. 11, 1981

[51] Int. Cl.$^3$ .............................................. C12P 7/24
[52] U.S. Cl. .................................................. 435/147
[58] Field of Search ............................... 435/147, 189

[56] References Cited

PUBLICATIONS

Prescott, S. C. et al., Industrial Microbiology, (1959), pp. 428–469.

*Primary Examiner*—Lionel M. Shapiro
*Attorney, Agent, or Firm*—Roman Saliwanchik

[57] ABSTRACT

Novel processes for preparing the useful chemical glyceraldehyde. This compound can be prepared by contacting glycerol with the enzyme methanol dehydrogenase. The enzyme can be in the pure form or crude form. Glycerol also can be converted to glyceraldehyde by contacting it with a methanol dehydrogenase-producing bacterium.

9 Claims, No Drawings

PROCESS FOR PREPARING GLYCERALDEHYDE FROM GLYCEROL WITH METHANOL DEHYDROGENASE

DESCRIPTION

BACKGROUND OF THE INVENTION

Glyceraldehyde is an industrially important chemical compound used by manufacturers of cosmetic products. It is currently produced by an osmium tetroxide-catalyzed conversion of acrolein to glyceraldehyde; however a problem of osmium recovery is encountered with this process.

Microorganisms capable of oxidizing a hydroxyl group of a polyalcohol molecule to form a keto compound are well documented, for example glycerol to dihydroxyacetone. However, this oxidation reaction is limited to the secondary alcohol function of the substrate. For example, dihydroxyacetone can be produced from glycerol using Acetobacter or Gluconobacter species. [Prescott, S. C. and C G. Dunn, 1959. Industrial Microbiology, McGraw Hill Book Co., Inc., New York, "The Acetic Acid Bacteria and Some of Their Biochemical Activities," pp. 428–469.]

The subject invention processes are the only known processes for preparing glyceraldehyde without the use of potentially carcinogenic reagents. This desirable feature is achieved by use of a natural enzyme, methanol dehydrogenase, acting upon glycerol. The enzyme can be used in the pure or crude forms. Also, the subject invention encompasses the use of a microbial process to convert glycerol to glyceraldehyde.

BRIEF SUMMARY OF THE INVENTION

Upon contacting methanol dehydrogenase with glycerol, there is obtained glyceraldehyde. The methanol dehydrogenase can be in a crude or pure form. Further, a microbial process using a methanol dehydrogenase-producing microbe can be the method for contacting the enzyme with glycerol to produce glyceraldehyde.

DETAILED DESCRIPTION OF THE INVENTION

The Enzyme

Methanol dehydrogenase (E.C. 1.1.99.8) has been purified from *M. organophilum* and from several methylotrophic bacteria and is apparently present in all procaryotes capable of growth on methane or methanol. The enzyme's physiological function is the oxidation of methanol to formaldehyde. Biochemical studies have shown the enzyme has a subunit molecular weight of approximately 60,000; most purified forms have total molecular weights in the range of 120,000 and 140,000. Enzymatic activity in vitro is dependent on the presence of an artificial electron carrier like phenazine methosulfate (PMS); ammonia or a methylated amine is required for activity when the enzyme is purified aerobically. Nicotinamide adenine dinucleotide (NAD+) is not reduced. The reaction catalyzed is a 2-step oxidation and can be represented as $RCH_2OH + PMS \rightarrow RCHO + PMSH_2$ and $RCHO + PMS + H_2O \rightarrow RCOOH + PMSH_2$ where R is hydrogen or an alkyl group. The enzyme exhibits broad substrate specificity for primary alcohols and oxidizes formaldehyde to formate. The purified enzyme has a high pH optimum for activity (pH 9–11).

The state of the art is such that knowing methanol dehydrogenase oxidizes methanol and other primary aliphatic alcohols would not suggest the enzyme could recognize a polyalcohol molecule as a substrate. Further, there is no disclosure or any suggestion that *M. organophilum* or any other methylotrophic bacteria could be used to convert glycerol in a one-step oxidation and permit the accumulation of this oxidation product, glyceraldehyde.

Methanol Dehydrogenase-Producing Microbes

Species of several genera are suitable to use as a source of methanol dehydrogenase in the microbiological conversion of glycerol to glyceraldehyde. These genera are included in the family Methylomonodaceae described below. Some members of the genus Pseudomonas (Family Pseudomonoadaceae) that can utilize methanol as the sole carbon and energy for growth can also be used. The preferred microorganism is *Methylobacterium organophilum*, NRRL B-12486.

*M. organophilum*, NRRL B-12486 has been deposited in the permanent collection at the Northern Regional Research Laboratory, U.S. Department of Agriculture, Peoria, Ill., U.S. It is a known microorganism which is also available from the American Type Culture Collection, ATCC, where its accession is ATCC 27886. These cultures can be obtained from these sources upon request thereto.

The study of methylotrophic bacteria has only been undertaken recently. The first major publication describing these microorganisms was published by Whittenbury et al. in 1970. [Whittenbury, R., K. C. Phillips and J. F. Wilkinson. 1970. Enrichment, Isolation and Some Properties of Methane-utilizing Bacteria. J. Gen. Microbiol. 61:205–218.] No definitive publication has appeared which adequately describes and characterizes the entire group of bacteria that grow on one carbon compounds, such as methane and methanol. *Bergey's Manual of Determinative Bacteriology*, 8th edition, published in 1974, does recognize the family Methylomonadaceae, but includes only a small portion of the species of methane-oxidizing bacteria that have been isolated during various experimental studies.

The following tentative classification scheme has been suggested for methane-oxidizing bacteria. [Colby, John, Howard Dalton and Roger Whittenbury. 1979. Annual Review of Microbiology, Vol. 33, Annual Reviews Inc., Palo Alto, Calif. "Biological and Biochemical Aspects of Microbial Growth on $C_1$ Compounds," pp. 481–517.]

Family Methylomonadaceae

Gram-negative bacteria utilizing methane as a growth substrate, may also utilize other 1-carbon compounds, such as methanol or methylamine.

Type I: Intracytoplasmic membranes arranged in bundles of vesicular discs, resting stage as Azotobacter-like cyst, ribulose monophosphate pathway for carbon assimilation, incomplete tricarboxylic acid cycle, obligate one-carbon organic compound utilizers.
  Subgroup A:
    DNA base ratio of 50–54% G+C, NAD or NADP dependent isocitrate dehydrogenase, rod or coccus shaped cells.
    Genus: Methylomonas
  Subgroup B:

autotrophic $CO_2$ fixation, DNA base ratio of 62.5–63.3% G+C, NAD dependent isocitrate dehydrogenase, coccus shape.

Genus: Methylococcus

Type II:
 Intracytoplasmic membranes arranged as pairs around cell periphery, exospores or lipid cysts, serine pathway for formaldehyde fixation for carbon assimilation, complete TCA cycle.

Subgroup A:
 obligate methanotrophs (use only 1C compounds as growth substrates). DNA base ratio of 62.5% G+C or greater where tested, NADP dependent isocitrate dehydrogenase.

Genera: Methanomonas, Methylosinus, and Methylocystis.

Subgroup B:
 Facultative methanotrophs (use a variety of more complex organic compounds as growth substrates in addition to 1C compounds). DNA base ratio 62.5% G+C or greater. NADP dependent isocitrate dehydrogenase.

Genus: Methylobacterium

In addition to these bacteria which can use methane as the sole carbon and energy source for growth, a group of bacteria also exist that can utilize methanol as a growth substrate. These bacteria share many morphological, physiological, and biochemical characteristics of the genus Methylobacterium.

Description: Gram-negative aerobic rods, generally pink-pigmented, DNA base ratio 60–65% G+C. Serine pathway for formaldehyde fixation during growth on 1C compounds. Growth on methanol, formaldehyde, sugars, tricarboxylic acids. No growth on methane. Currently, it is felt these bacteria should be assigned to a restricted group in the family Pseudomonadaceae, Genus Pseudomonas. The only characteristic distinguishing them from other pseudomonads is the ability to grow on methanol. Examples of these organisms are Pseudomonas 3A2, Pseudomonas AM1, Pseudomonas M27, Pseudomonas PRL-W4.

Microbial Procedure for Preparing Methanol Dehydrogenase

The microorganisms are grown in a conventional aqueous mineral salts medium containing:

(a) a source of nitrogen such as nitrate salts, nitrite salts, ammonium salts, nitrogen gas or organic nitrogen compounds (urea, yeast extract, casamino acids), (b) ions such as sodium, potassium, iron, calcium, magnesium, phosphate and sulfate, (c) trace elements like manganese, zinc, copper, molybdenum, cobalt, borate in levels supplied by tap water, (d) a source of carbon such as methane or methanol. Additionally, *M. organophilum* and the facultative methanol-utilizers can be grown on mono- and disaccharides, tricarboxylic acid cycle intermediates, or broth rich in organic nutrients. Methanol is the preferred substrate.

The organisms require oxygen present in the atmosphere for growth. The temperature range for growth is 5°–55° C. with an optimum of 28°–31° C. for *M. organophilum*. The organisms will grow in media having a pH in the range of 5.5–8.5, preferably around neutral pH.

Methanol dehydrogenase is synthesized in high levels by cells grown on methane or methanol. To increase the low enzyme levels found in cells grown on more complex organic substrates, methanol is added to the culture medium at any stage of growth as an inducer of enzyme synthesis.

Several types of preparations can be used to supply methanol dehydrogenase activity for the bioconversion, including whole cells, cell-free extracts or partially purified enzyme. Whole cell preparations may be used directly from the growth medium, harvested, stored by freezing or drying or immobilized. The cells may be immobilized by standard techniques, such as entrapment within polyacrylamide or covalent coupling of the cells to a polyelectrolyte carrier as described in *Methods in Microbiology*, Vol. XLIV, 1976, Academic Press, Inc., New York. pp 11–317. Cell-free extracts and partially purified enzyme are prepared from cells that are harvested, washed, resuspended in an aqueous medium and disintegrated by conventional techniques. These can include sonication, grinding or shaking with abrasives, osmotic shock, or disruption by pressure in a French pressure cell. The released enzymes dissolve in this medium, which may be a weak solution of a phosphate salt, a zwitterionic amino acid (N-substituted taurines or glycine), a cationic primary aliphatic amine, or tris(hydroxymethyl)aminomethane with a range of pH 6.0 to pH 10, preferably pH 7.0. This suspension or the suspension obtained after removal of cell debris represents a crude extract.

Further purification of the methanol dehydrogenase may be accomplished using standard biochemical protein purification techniques such as centrifugation, acid precipitation, ammonium sulfate precipitation, gel filtration, ultrafiltration, or ion exchange chromatography.

Bioconversion process: The bioconversion of glycerol to glyceraldehyde is accomplished by exposing the enzyme methanol dehydrogenase to glycerol in an aqueous medium. The medium is a weakly buffered solution with a pH in the range of 5–11 that contains 0–20% glycerol. The bioconversion mixture is incubated for 0–7 days at a temperature in the range of 5°–50° C. During incubation, the mixture has access to atmospheric oxygen and is preferably stirred. Peak production of glyceraldehyde occurs early during the bioconversion. Conversion of 35% of the glycerol present has been observed.

Examples of various procedures that can be used include:

(1) Direct addition of glycerol to the growing culture of organisms. Optimum conditions are the same as for growth plus the addition of 5% glycerol. Peak production of glyceraldehyde occurs within 2 days.

(2) Inoculation of a bioconversion medium containing 0–20% (w/v) glycerol with whole cells in various forms, such as a direct inoculum from a culture, resuspension of harvested, frozen, dried or immobilized cells. Optimum conditions for *M. organophilum* include using a weakly buffered aqueous medium of neutral pH containing 5% glycerol at 32°–37° C.

(3) Addition of glycerol to a crude extract. Inclusion of an ammonium salt (0.1–20 mM) and an artificial electron acceptor such as phenazine methosulfate (0–2 mM) stimulate the conversion.

(4) Resuspension of a partially purified enzyme preparation in a weakly buffered solution, pH 6.0–10.5, containing glycerol, an ammonium salt (0–50 mM) and an artificial electron acceptor. The optimum pH for the conversion is pH 7–9. The ammonium salt is not required; however it will stimulate activity.

Following are examples which illustrate the subject invention process. These examples are merely illustrative, and, thus, should not be construed as limiting. All percentages are by weight and all solvent mixture proportions are by volume unless otherwise noted.

EXAMPLE 1

*Methylobacterium organophilum*, NRRL B-12486, is grown in a mineral salts medium (NMS) [Patt, T. E., G. C. Cole, J. Bland and R. S. Hanson, 1974. Isolation and Characterization of Bacteria that Grow on Methane and Organic Compounds as Sole Sources of Carbon and Energy, J. Bacteriol. 120:955-964] with 0.25% filter-sterilized methanol added as the sole carbon and energy source for growth. The cultures are incubated at 30° C. on a rotary shaker.

Cultures that are to be used to assay glycerol-oxidizing activity by cell-free extracts or by resting cell suspensions are harvested in the middle of the exponential phase growth by low speed centrifugation at 4° C., washed three times with cold 30 mM $KPO_4$ buffer pH 7.2 and frozen at $-20°$ C.

Cultures that are used in shake flask bioconversion experiments are grown to late exponential phase of growth and used directly as inoculum or are harvested by low speed centrifugation, washed once with 50 mM $KPO_4$ buffer pH 7.0 and resuspended in NMS medium to their original cell concentration.

EXAMPLE 2

Bioconversion of Glycerol to Glyceraldehyde

A series of 500 ml Erlenmeyer flasks, each containing 100 ml of bioconversion medium, are autoclaved at 121° C. for 30 minutes. Prior to inoculation, the medium is adjusted to about pH 6.9.

The bioconversion medium consists of a liquid base of NMS medium plus (per liter): 3 g $NH_4Cl$, 3 g $CaCO_3$, 1 g Amberex 1003 (Amber Laboratories) and 50 g glycerol technical grade.

Each flask is inoculated with 5-20% inoculum of cell cultures or resuspended washed cells of a methanol dehydrogenase-producing microbe, e.g. *M. organophilum*, NRRL B-12486. The flasks are then incubated on a rotary shaker at 31° C. for 3 days.

Using the above-described process, up to 35% of the glycerol is converted to glyceraldehyde in 24 hours.

The accumulated glyceraldehyde can be recovered from the bioconversion medium as an aqueous solution of glyceraldehyde or as a syrup containing glyceraldehyde plus unconverted glycerol. The aqueous solution is prepared by removing the solids from the bioconversion beer by such techniques as filtration or centrifugation. The cleared beer contains predominantly glyceraldehyde and residual glycerol. This may be concentrated to the desired glyceraldehyde content or to a syrup by evaporation or freeze-drying at temperatures less than 40° C.

EXAMPLE 3

Glycerol can be converted to glyceraldehyde by contacting the glycerol with crude or pure methanol dehydrogenase. Basically, this process can be carried out as follows:

Frozen cells of *M. organophilum* (6 g) are thawed and resuspended in 15 ml of cold 50 mM phosphate buffer pH 7.0. The suspension is disrupted by three passes through a French pressure cell at 18,000 $lb/in^2$. This preparation is centrifuged at $20,000 \times g$ for 15 min at 4° C. A 1 ml sample of the resultant crude extract ($\sim$25-30 mg protein/ml) is added to a 500 ml Erlenmeyer flask containing 50 ml of 10 mM Tris-HCl buffer pH 8.0 and 20 mM $NH_4Cl$. Phenazine methosulfate (10 mg) and glycerol (5 g) are added to the flask. The flask is incubated at 31° C. for 2 days on a rotary shaker. A glyceraldehyde level of greater than 1 g/liter is observed within 16 hours.

EXAMPLE 4

Use of Immobilized Cells

Cells of *M. organophilum* (5 g wet weight) are suspended in cold 50 mM tris-HCl buffer pH 7.5 to a final volume of 25 ml. The suspension is mixed rapidly with 23 ml of the same buffer containing 7.23 g acrylamide and 0.37 g N,N'-methylene bis(acrylamide). One ml of 10% N,N,N',N'-tetramethylenediamine and one ml of 5% ammonium persulfate are added to polymerize the gel. The mixture is poured into a polymerization vessel and kept cool throughout polymerization. The gel is cut into 1 mm cubes and an amount equivalent to 1 g wet weight cells is used to run the bioconversion under condtions described in Example 2. Glyceraldehyde was detected in the beer after one day incubation.

I claim:

1. A process for preparing glyceraldehyde which comprises contacting glycerol with methanol dehydrogenase until a substantial amount of glyceraldehyde is produced, and recovering the glyceraldehyde.

2. A process, according to claim 1, wherein said methanol dehydrogenase is used as a partially purified enzyme obtained from a methylotrophic bacterium.

3. A process, according to claim 2, wherein said methylotrophic bacterium is *Methylobacterium organophilum*, NRRL B-12486.

4. A process, according to claim 1, wherein said methanol dehydrogenase is present in a cell-free extract of a methylotrophic bacterium and said extract is used in the process to prepare glyceraldehyde.

5. A process, according to claim 4, wherein said methylotrophic bacterium is *Methylobacterium organophilum*, NRRL B-12486.

6. A microbiological process for preparing glyceraldehyde which comprises cultivating a methylotrophic bacterium, and contacting said bacterium with glycerol until a substantial amount of glyceraldehyde is produced, and recovering the glyceraldehyde.

7. A process, according to claim 6, wherein said methylotrophic bacterium is *Methylobacterium organophilum*, NRRL B-12486.

8. A microbiological process for preparing glyceraldehyde which comprises cultivating a methanol dehydrogenase-producing microbe and contacting said bacterium with glycerol until a substantial amount of glyceraldehyde is produced, and recovering the glyceraldehyde.

9. An immobilized cell process for preparing glyceraldehyde which comprises contacting glycerol with said immobilized cell containing methanol dehydrogenase until a substantial amount of glyceraldehyde is produced, and recovering the glyceraldehyde.

* * * * *